United States Patent [19]

Sato et al.

[11] Patent Number: 5,463,133
[45] Date of Patent: Oct. 31, 1995

[54] PHENETHYL ALCOHOL DERIVATIVE AND RECORDING MATERIAL CONTAINING THE SAME

[75] Inventors: Takehiro Sato, Kanagawa; Kimiaki Kinosita, Saitama; Minoru Kaeriyama, Kanagawa; Tomoya Hidaka, Chiba, all of Japan

[73] Assignee: Nippon Soda Co., Ltd., Tokyo, Japan

[21] Appl. No.: 244,563

[22] PCT Filed: Sep. 27, 1993

[86] PCT No.: PCT/JP93/01368

§ 371 Date: May 31, 1994

§ 102(e) Date: May 31, 1994

[87] PCT Pub. No.: WO94/07832

PCT Pub. Date: Apr. 14, 1994

[51] Int. Cl.$^6$ .................... C07C 31/08; C07C 317/14
[52] U.S. Cl. .................... 568/33; 568/53; 568/333; 568/636; 568/638; 568/640; 568/641; 568/44; 568/48; 568/306; 568/586
[58] Field of Search .................... 568/33, 53, 333, 568/638, 636, 640, 641, 44, 48, 306, 586

[56] References Cited

U.S. PATENT DOCUMENTS

| | | | |
|---|---|---|---|
| 4,288,631 | 9/1981 | Ching | 568/333 |
| 4,691,059 | 9/1987 | Mitra et al. | 568/333 |
| 5,258,410 | 11/1993 | Shuto et al. | 568/640 |

FOREIGN PATENT DOCUMENTS

| | | | |
|---|---|---|---|
| 58-180634 | 5/1983 | Japan | 568/33 |
| 84-2882 | 8/1984 | WIPO | 568/33 |

*Primary Examiner*—James H. Reamer
*Attorney, Agent, or Firm*—Jacobson, Price, Holman & Stern

[57] ABSTRACT

The present invention is to provide phenethyl alcohol derivative represented by the general formula (I), which is a stabilizing agent for colored images, particularly improved in resistance to plasticizers for the use in recording materials.

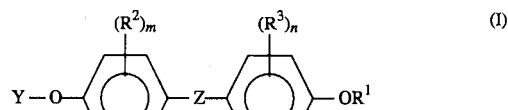

(I)

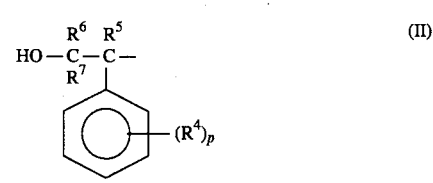

(II)

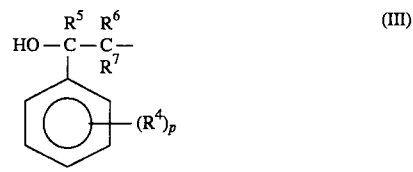

(III)

(wherein Y: formula (II) or formula (III)
$R^1$: H, alkyl, aralkyl
$R^2$, $R^3$ and $R^4$: halogen, nitro, alkyl, alkoxy, alkenyl, alkenyloxy,
$R^5$, $R^6$ and $R^7$: H, alkyl,
Z: —$SO_2$—, —CO—, —$C(CH_3)_2$—, —S—, —O—
m, n and p: 0, integer)

7 Claims, No Drawings

PHENETHYL ALCOHOL DERIVATIVE AND RECORDING MATERIAL CONTAINING THE SAME

This application is a 371 of PCT/JP93/01368, Sep. 27, 1993.

FIELD OF THE INVENTION

The present invention relates to a phenethyl alcohol derivative and a recording material comprising the compound, which is superior in long term stabilizing property for the colored images.

BACKGROUND OF THE INVENTION

Recording materials to which the principle of color development resulting from a reaction between a leuco chromogen and a color developer is applied have been widely used for thermal sensitive recording papers for output recordings by facsimiles, printers or the like or pressure sensitive copy papers for slip books simultaneously transcribing multiple sheets, because such recording materials can be recorded by using a simpler recording apparatus in a short time without undergoing any troublesome procedures such as development, fixing, etc.

It is desired for the recording materials described above, the one which can develop color faster, retain clear whiteness of the uncolored area (hereinafter represented as "background"), and provide high toughness in the developed images and the background. Recently, a great amount of recording materials have been consumed particularly in a field such as labeling where the reliability of recorded images is critically demanded. Accordingly, the recording materials capable of providing colored images being stable in long term to plasticizers and fat and oils those are contained in the organic macromolecules used as packaging materials has been intensively desired. Many efforts have been made to provide such recording material from various points of view, such as leuco chromogen, color developing agent, addition of stabilizer, etc. Nevertheless, the material with desired properties mentioned above has not been developed.

Diphenyl sulfone derivatives are known as useful as a recording material similar to the compound of the present invention. They are well known as a color developer used for recording materials. Diphenyl sulfone derivatives one of which phenyl is substituted with alkoxy or aralkyloxy and the other phenyl is substituted with hydroxyl are proposed as a color developer in Japanese Patent Laid-opened No. Sho 57-210886, No. Sho 58-20493, No. Sho 58-82788, No. Sho 58-132593, and No. Sho 60-13852, and World Open WO 84/02882. However, any of them are not sufficient in the stabilizing property for the developed images.

For improving the long term stability of the colored images described above, many patent applications covering the recording materials comprising a epoxy group such as novolac epoxy resin or glycydyl compound have been filed. The applicant of the present invention has also filed a patent application (World open WO 93/06074) wherein 4-hydroxy-4'-(2-methylglycydyloxy)diphenyl sulfone is disclosed as a recording material. However, all of the recording materials disclosed in the patent applications described above are not sufficient yet for the practical use in terms of staining of the background and the long term stability of the colored images.

As described above, in recent years, improvement in long term stability of the colored images developed on the recording material, particularly improvement in resistance to plasticizers have particularly been expected. It is an object of the present invention to provide a recording material superior in giving long term stability of colored image which can thereby solve the problems described above.

Disclosure of the Invention

The present invention is directed to a recording material comprising at least one or more phenethyl alcohol(s) or the derivative(s) thereof represented by the following general formula (I):

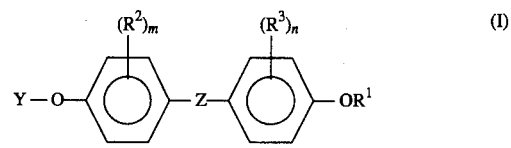

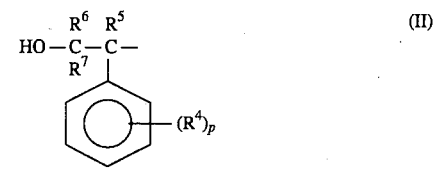

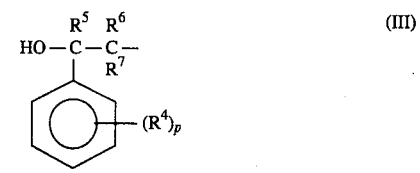

(wherein Y is a substitute represented by the general formula (II) or (III), $R^1$ is hydrogen, lower alkyl or optionally substituted aralkyl, $R^2$, $R^3$ and $R^4$ are each independently halogen, nitro, lower alkyl, lower alkoxy, lower alkenyl, or lower alkenyloxy, $R^5$, $R^6$ and $R^7$ are independently hydrogen or lower alkyl, Z is —$SO_2$—, —CO—, —$C(CH_3)_2$—, —S—, or —O—, m, n and p independently denotes an integer 0, 1, 2, 3 or 4, with the proviso that the substitutes represented by $R^2$, $R^3$ and $R^4$ may be different from one another when m, n and p are independently an integer of 2 or more.)

Insofar as the substituents in the general formula (I), each of lower alkyl, lower alkoxy, lower alkenyl and lower alkenyloxy are independently the one containing 1 to 5 carbon atom(s) which is optionally substituted by a side chain or side chains. The optionally substituted aralkyl denotes benzyl or phenethyl optionally containing a substituent or substituents at the benzene ring, wherein the substituent is halogen, nitro, optionally substituted alkyl by a side chain containing 1 to 5 carbon atom(s), optionally substituted alkoxy by a side chain containing 1 to 5 carbon atom(s) or the like.

In the following, the examples of phenethyl alcohol derivatives represented by the general formula (I), however, the derivatives should not be limited to those examples.

The examples of phenethyl alcohol derivatives of the formula (I) wherein Y contains a group represented by the general formula (II) are illustrated in Table 1, while the examples of phenethyl alcohol derivatives of the formula (I) wherein Y contains a group represented by the general formula (III) are illustrated in Table 2.

TABLE 1

Formula (II):
$$Y = HO-\underset{R^7}{\underset{|}{C}}-\overset{R^6}{\underset{|}{C}}- \text{ with phenyl bearing } (R^4)_p$$
(with $R^5$ on the first C)

Formula (I):
$$Y-O-\text{Ar}(R^2)_m-Z-\text{Ar}(R^3)_n-OR^1$$

*The horizontal bar indicates no substituent but hydrogen at the position.

| Compound No. | $R^1$ | $(R^2)_m$ | $(R^3)_n$ | $(R^4)_p$ | $R^5$ | $R^6$ | $R^7$ | Z | Melting Point °C. |
|---|---|---|---|---|---|---|---|---|---|
| 1-1 | H | — | — | — | H | H | H | $-SO_2-$ | 195–197 |
| 1-2 | $-CH_2C_6H_5$ | — | — | — | H | H | H | $-SO_2-$ | 120–122 |
| 1-3 | $-CH_3$ | — | — | — | H | H | H | $-SO_2-$ | |
| 1-4 | $-i-C_3H_7$ | — | — | — | H | H | H | $-SO_2-$ | |
| 1-5 | $-CH_2C_6H_5$ | — | — | — | $-CH_3$ | H | H | $-SO_2-$ | |
| 1-6 | $-CH_2C_6H_5$ | — | — | $4-OC_2H_5$ | H | H | H | $-SO_2-$ | |
| 1-7 | H | $3-CH_3$ | $3-CH_3$ | — | H | H | H | $-SO_2-$ | |
| 1-8 | H | $3,5-(CH_3)_2$ | $3,5-(CH_3)_2$ | — | H | H | H | $-SO_2-$ | |
| 1-9 | H | $3-CH_2CH=CH_2$ | $3-CH_2CH=CH_2$ | — | H | H | H | $-SO_2-$ | |
| 1-10 | H | $3,5-(Br)_2$ | $3,5-(Br)_2$ | — | H | H | H | $-SO_2-$ | |
| 1-11 | H | $3,5-(Br)_2$ | $3,5-(Br)_2$ | $4-CH_3$ | H | H | H | $-SO_2-$ | |
| 1-12 | H | — | — | $4-CH_3$ | H | H | H | $-SO_2-$ | |
| 1-13 | H | — | — | $2-CH_3$ | H | H | H | $-SO_2-$ | |
| 1-14 | H | — | — | $4-C_2H_5$ | H | H | H | $-SO_2-$ | |
| 1-15 | H | — | — | $4-i-C_3H_7$ | H | H | H | $-SO_2-$ | |
| 1-16 | H | — | — | $4-n-C_3H_7$ | H | H | H | $-SO_2-$ | |
| 1-17 | H | — | — | $4-OCH_3$ | H | H | H | $-SO_2-$ | |
| 1-18 | H | — | — | $4-Cl$ | H | H | H | $-SO_2-$ | |
| 1-19 | H | — | — | $4-Br$ | H | H | H | $-SO_2-$ | |
| 1-20 | H | — | — | $4-CH_3$ | $-CH_3$ | H | H | $-SO_2-$ | |
| 1-21 | H | — | — | $2-CH_3$ | $-CH_3$ | H | H | $-SO_2-$ | |
| 1-22 | H | — | — | $4-C_2H_5$ | $-CH_3$ | H | H | $-SO_2-$ | |
| 1-23 | H | — | — | $4-n-C_3H_7$ | $-CH_3$ | H | H | $-SO_2-$ | |
| 1-24 | H | — | — | $4-i-C_3H_7$ | $-CH_3$ | H | H | $-SO_2-$ | |
| 1-25 | H | — | — | $4-OCH_3$ | $-CH_3$ | H | H | $-SO_2-$ | |
| 1-26 | H | — | — | $4-OC_2H_5$ | $-CH_3$ | H | H | $-SO_2-$ | |
| 1-27 | H | — | — | $4-Cl$ | $-CH_3$ | H | H | $-SO_2-$ | |
| 1-28 | H | — | — | $4-Br$ | $-CH_3$ | H | H | $-SO_2-$ | |
| 1-29 | H | — | — | $2-Cl$ | $-CH_3$ | H | H | $-SO_2-$ | |
| 1-30 | H | — | — | $4-NO_2$ | H | H | H | $-SO_2-$ | |
| 1-31 | H | — | — | $4-NO_2$ | $-CH_3$ | H | H | $-SO_2-$ | |
| 1-32 | H | — | — | — | $-CH_3$ | H | H | $-SO_2-$ | |
| 1-33 | H | — | — | — | $-CH_3$ | $-CH_3$ | H | $-SO_2-$ | |
| 1-34 | H | — | — | — | $-CH_3$ | $-CH_3$ | $-CH_3$ | $-SO_2-$ | |
| 1-35 | H | — | — | — | $-C_2H_5$ | H | H | $-SO_2-$ | |
| 1-36 | H | — | — | — | H | H | H | $-CO-$ | 57–60 |
| 1-37 | H | — | — | — | $-CH_3$ | H | H | $-CO-$ | |
| 1-38 | $-CH_2C_6H_5$ | — | — | — | H | H | H | $-CO-$ | |
| 1-39 | H | — | — | $4-CH_3$ | H | H | H | $-CO-$ | |
| 1-40 | H | — | — | $4-CH_3$ | $-CH_3$ | H | H | $-CO-$ | |
| 1-41 | H | — | — | $4-C_2H_5$ | $-CH_3$ | H | H | $-CO-$ | |
| 1-42 | H | — | — | $4-OCH_3$ | H | H | H | $-CO-$ | |
| 1-43 | H | — | — | $2-Cl$ | H | H | H | $-CO-$ | |
| 1-44 | H | — | — | $4-Br$ | H | H | H | $-CO-$ | |
| 1-45 | H | — | — | — | H | H | H | $-C(CH_3)_2-$ | |
| 1-46 | $-CH_2C_6H_5$ | — | — | — | H | H | H | $-C(CH_3)_2-$ | |
| 1-47 | H | — | — | $4-CH_3$ | $-CH_3$ | H | H | $-C(CH_3)_2-$ | |
| 1-48 | H | — | — | $4-C_2H_5$ | $-CH_3$ | H | H | $-C(CH_3)_2-$ | |
| 1-49 | H | — | — | — | $-CH_3$ | H | H | $-C(CH_3)_2-$ | |
| 1-50 | H | — | — | — | H | H | H | $-O-$ | |
| 1-51 | $-CH_2C_6H_5$ | — | — | — | H | H | H | $-O-$ | |
| 1-52 | H | — | — | $4-CH_3$ | $-CH_3$ | H | H | $-O-$ | |
| 1-53 | H | — | — | $4-C_2H_5$ | $-CH_3$ | H | H | $-O-$ | |
| 1-54 | H | — | — | — | $-CH_3$ | H | H | $-O-$ | |
| 1-55 | H | — | — | — | H | H | H | $-S-$ | |
| 1-56 | $-CH_2C_6H_5$ | — | — | — | H | H | H | $-S-$ | |
| 1-57 | H | — | — | $4-CH_3$ | $-CH_3$ | H | H | $-S-$ | |
| 1-58 | H | — | — | $4-C_2H_5$ | $-CH_3$ | H | H | $-S-$ | |

There are several methods for manufacturing phenethyl alcohol derivatives represented by the formula (I), which depend upon the raw materials to be used for the manufacturing thereof. When styrene oxide derivatives are used as a raw material, for example, the phenethyl alcohol derivatives can be manufactured according to the method illustrated in the following reaction formula.

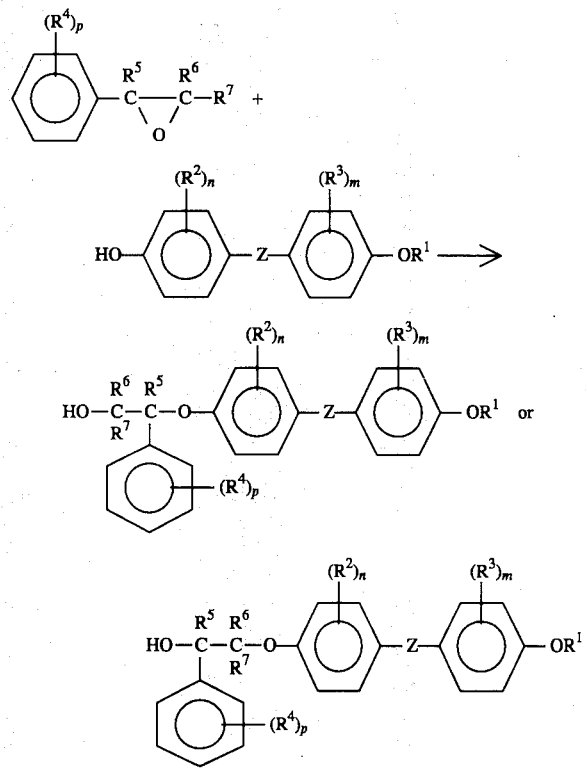

(wherein all of the substituents in the formulas are as defined above.)

Two examples of the method described above are supplied as follows.

The one method comprises a reaction conducted in a bilayer solvent comprising water and water-insoluble organic solvent, for example, aromatic solvents, such as toluene, chlorobenzene and dichlorobenzene; ketones, such as methyl isobutyl ketone and diethyl ketone; and esters such as acetate, in the presence of an inorganic alkaline substance, such as sodium hydroxide, potassium hydroxide, lithium hydroxide, sodium carbonate, potassium carbonate and lithium carbonate at the reaction temperature in a range of from 80° C. to 95° C. for several to 10 and several hours.

The other method comprises a reaction conducted in an organic solvent such as toluene, methyl ethyl ketone, methyl isobutyl ketone, acetone, dimethylsulfoxide and dimethyl formamide, in the presence of catalytic tertiary amines such as triethanolamine, triisopropanolamine, triethylamine, N,N-dimethylbenzylamine, N,N-dimethylaniline, N-benzyl-N-ethylaniline and N,N-diethylorthotoluidine at the reaction temperature in a range of from 60° C. to 180° C. for several to 10 and several hours.

In general, the formations of two compounds containing substituents represented by the formula (II) and the formula (II) depend upon the position where the epoxy group in each styrene oxide derivative is cleaved to react. However, the relative ratio in the formation of both compounds can be changed by controlling the reaction conditions such as reaction temperature, solvents used, catalysts or the like, and highly purified compounds can be obtained by the selective extraction with a solvent.

The compounds of the present invention manufactured according to the method described above form the crystals in different shapes or the addition products with the solvent used depending upon the conditions at precipitating the crystals, for example, a type of solvent and temperature for precipitation. Such result can be confirmed by checking the melting point of the crystals and from the analysis by infrared spectroscopy, X-ray diffraction and other applicable means.

It is noteworthy that the compound of the present invention can be used not only as an image stabilizing agent with resistance to plasticizers for preventing decolorization of the image caused by a plasticizer, but also as a color developer having excellent resistance to plasticizers when the compound contains a benzene ring substituted by hydroxy wherein the substituent $R^1$ is hydrogen.

With the compound of the present invention, the recording material containing a leuco chromogen can be manufactured by customary methods in the art. When using the compound of the invention as an image stabilizing agent, it is used together with a color developer, various sensitizers and adjuvants, while it is used together with various sensitizers and adjuvants when using it as a color developer. Naturally, it is possible to use one compound as an image stabilizing agent and the other as a color developer by combining a plurality of the compounds of the present invention. It is also possible to produce a recording material capable of providing a specific characteristic in color development by combining the compound of the present invention with a compound having similar use purpose.

It is very beneficial to provide the compound of the present invention having a property applicable for both usages of an image stabilizing agent and a color developer, since it allows to manufacture at a low cost by diminishing the relative total amounts of both the image stabilizing agent and the color developer used relatively to the amount of a leuco chromogen used.

The compounds of the present invention are applicable to any recording materials as far as the recording material uses a leuco chromogen. For example, the compounds are applicable to thermal sensitive recording papers, pressure sensitive copying papers, etc.

When the compound of the present invention is used for thermal sensitive recording papers, they are allowed to be processed according to a method similar to that for known image stabilizing agents or color developers. For example, the recording material can be manufactured by dispersing each of the compound of this invention and a leuco chromogen in aqueous solution of a water-soluble binder, mixing each suspensions, coating the mixture on a holding material such as paper, then drying the coated paper. The compound of the invention may be contained in a color developing layer as hereinbefore described, however, it may also be contained in any layer such like a protecting layer if the recording papers is constructed in multilayer structure. In this case, if the compound of this invention is used as an image stabilizing agent, the ratio of the amount thereof relatively to the amount of a leuco chromogen is 0.1~5 parts by weight, preferably 0.2~2 parts by weight based on 1 part by weight of a leuco chromogen. If the compound is used for a color developer, the ratio of the amount thereof is 1~10 parts by weight, preferably 1.5~5 parts by weight based on 1 part by weight of a leuco chromogen. Other color developers, image stabilizing agents, sensitizing agents, fillers, dispersing agents, antioxidants, antisensitizing agents, antistickers, antifoaming agents, photo-stabilizing agents and fluorescent brightening agents, etc. may be added into the dispersion, if necessary.

For a leuco chromogen used for the recording materials of the present invention, leuco dyes comprising each of fluoranes, phthalides, lactums, triphenyl methanes, phenothiazines, spiropyranes, etc. are exemplified. However, the recording materials specified in the present invention should not be limited to the leuco dyes described above, any leuco chromogen which develop a color when it contacted to a color developer of an acidic substance are applicable. Among the leuco dyes exemplified above, the following fluorane compounds are further supplied as examples.
3-diethylamino-6-methyl-7-anilinofluorane,
3-dibutylamino-6-methyl-7-anilinofluorane,
3-(N-ethyl-N-isobutylamino)-6-methyl-7-anilinofluorane,
3-(N-methyl-N-propylamino)-6-methyl-7-anilinofluorane,
3-(N-ethyl-N-isopentylamino)-6-methyl-7-anilinofluorane,
3-diethylamino-7-(o-chloroanilino)-fluorane,
3-dibutylamino-7-(o-chloroanilino)-fluorane,
3-diethylamino-7-dibenzylaminofluorane,
3-diethylamino-5-methyl-7-dibenzylaminofluorane,
3-(N-ethyl-p-toluidino)-6-methyl-7-anilinofluorane,
3-(N-cyclohexyl-N-methylamino)-6-methyl-7-anilinofluorane,
3-(N-ethyl-N-isobutylamino)-5.6-benzofluorane,
3-pyrrolydino-6-methyl-7-anilinofluorane.
3-piperidino-6-methyl-7-anilinofluorane, and the like.

For a color developer used for thermal sensitive recording papers when the compound of this invention is used as an image stabilizing agent or further used by combining with an other color developer, the following examples are supplied and any can be optionally selected. The representative examples of the color developer includes bisphenol compounds, such as bisphenol A, 4,4'-sec-butylidene bisphenol, 4.4'-cyclohexylidene bisphenol, 2,2'-dihydroxydiphenyl and pentamethylene-bis(4-hydroxybenzoate); sulfur containing bisphenol compounds, such as 1,7-di(4-hydroxyphenylthio)-3,5-dioxaheptane; 4-hydroxybenzoates, such as benzyl 4-hydroxy benzoate, ethyl 4-hydroxy benzoate, propyl 4-hydroxy benzoate, isopropyl 4-hydroxy benzoate, butyl 4-hydroxy benzoate, isobutyl 4-hydroxy benzoate, chlorobenzyl 4-hydroxy benzoate, methylbenzyl 4-hydroxy benzoate and diphenylmethyl 4-hydroxy benzoate; metal salts of benzoic acid, such as zinc benzoate and zinc 4-nitro benzoate; hydroxydiphenyl sulfones, such as 4-hydroxy-4'-methyl diphenyl sulfone, 4-hydroxy-4'-isopropoxydiphenyl sulfone, 4-hydroxy-4'-butoxydiphenyl sulfone: 4-hydroxyphthalate diesters, such as dimethyl 4-hydroxy phthalate, dicyclohexyl 4-hydroxy phthalate and diphenyl 4-hydroxy phthalate; hydroxy naphthoate, such as 2-hydroxy-6-carboxy naphthalene, hydroxy acetophenone, p-phenyl phenol, benzyl 4-hydroxy phenyl acetate, p-benzyl phenol, hydroquinone monobenzylether and tribromoethyl sulfones, such as tribromoethyl phenyl sulfone, etc.

For the representatives of a sensitizer used for thermal sensitive recording papers when the compound of this invention is used in combining with a sensitizer, higher fatty acid amides, benzamides, stearic acid anilides, acetoacetic acid anilides, thioacetanilides, dibenzyl oxalate, dimethyl phthalate, dibenzyl telephthalate, dibenzyl isophthalate, bis-(tert-butylphenols), 4,4'-dihydroxydiphenyl sulfone diethers, 1,2-bis(phenoxy) ethane, 1,2-bis(4-methylphenoxy) ethane, 1,2-bis(3-methylphenoxy) ethane, 2-naphthol benzyl ether, diphenylamine, carbazole, 2,3-di-m-tolylbutane, 4-benzyl biphenyl, 4,4'-dimethyl biphenyl, m-terphenyl, di-beta-naphthyl phenylenediamine, etc. are exemplified.

For examples of a filler, clay, talc, kaolinite, satinwhite, titanium oxide, calcium carbonate, magnesium carbonate, barium sulfate, magnesium silicate, aluminum silicate, etc. are exemplified. For examples of a dispersing agent, sulfosuccinic acid esters such as sodium dioctyl sulfosuccinate, sodium dodecylbenzene sulfonate, sodium salt of lauryl alcohol sulfate ester, fatty acid salts, etc. are exemplified. For examples of a colored image stabilizing agent, salicylic acid derivatives, metal salts of oxynaphthoic acid derivatives (particularly zinc salt) and other water-insoluble zinc containing compounds, etc., are exemplified. For examples of an antioxidant. 2,2'-methylenebis(4-methyl- 6-tert-butylphenol), 2,2'-methylenebis(4-ethyl-6-tert-butylphenol), 4,4'-propylmethylenebis(3-methyl-6-tert-butylphenol), and 4,4'-thiobis(2-tert-butyl-5-methylphenol), etc. are exemplified. For examples of an antisensitizing agent, aliphatic higher alcohols, polyethylene glycols and guanidine derivatives, etc. are exemplified. For examples of an antisticker, stearic acid, zinc stearate, calcium stearate, carnauba wax, paraffin wax and ester wax, etc. are exemplified.

When the compound of this invention is used for the manufacture of pressure sensitive copying papers, the same methods which are used for known image stabilizing agents, color developers or sensititizers can be employed thereto. For example, a leuco chromogen micro-capsuled according to a customary method is dispersed by using a proper dispersing agent, then the dispersion is coated on the papers to prepare chromogenic sheets. On the other hand, the dispersion of a color developer is coated on the papers to prepare color developer sheets. At the preparation or both dispersions described above, the compound of this invention can be incorporated into the dispersion either of the leuco chromogen or the color developer, when the compound is used as an image stabilizing agent.

Then both sheets prepared as described above are combined to form pressure sensitive copying papers. A unit paper composed or an upper layer paper which is coated and impregnated with microcapsule enveloping the leuco chromogen solution in organic solvent over the lower surface thereof and a lower layer paper which is coated and impregnated with color developer over the upper surface thereof, or so called "self content paper" that is coated with said microcapsules and the color developer over the same surface of the papers are allowable to use as pressure sensitive copying papers.

BEST MODE FOR CARRYING OUT THE INVENTION

Now, the present invention is further described in detail with referring to the examples hereinbelow. However, the scope of the present invention should not be limited by the examples.

EXAMPLE 1

(Example of the synthesis of Compound 1—1)

To 250 ml of methyl isobutyl ketone were added 50g of 4, 4'-dihydroxydiphenyl sulfone, 16 g of styrene oxide and 1 ml of 80% triethanolamine, then the mixture was heated to reflux to react for 6 hours. After cooling the reacted mixture, the mixture was washed with saturated aqueous solution of sodium carbonate to remove the unreacted raw materials. Then the product was extracted with 300 ml of 4% aqueous solution of sodium hydroxide to separate the water layer. The water layer was acidified with 10% hydrochloric acid to obtain 20 g of the crude crystals. In the crystals, compounds having substituents represented by the formulas (II) and (III) are contained.

The crude crystals added with 150 ml of ethyl acetate were heated to reflux and cooled, then the precipitated crystals were filtered, affording 12 g of 4-(α-(hydroxymethyl)benzyloxy)-4'-hydroxydiphenyl sulfone having a substituent represented by the formula (II) in a form of whitish crystals, of which melting point is from 195° C. to 197° C.

EXAMPLE 2

(Example of the synthesis of Compound 2-1)

The filtrate obtained by removing the recrystallized objective compound of the Example 1 in the ethyl acetate solution by filtration was purified by column chromatography, affording 3.5 g of 4-(β-hydroxyphenetyloxy)-4'-hydroxydiphenyl sulfone having a substituent represented by the formula (III) in a form of whitish crystals, of which melting point is from 170° C. to 172° C.

EXAMPLE 3

(Example of the synthesis of Compounds 1-2 and 2—2)

To 250 ml of toluene were added 12 g of styrene oxide, 34 g of 4-benzyloxy-4'-hydroxydiphenyl sulfone and 3 ml of triethylamine, then the mixture was heated to reflux to react for 3 hours. After cooling the reacted mixture, the crude crystals precipitated therein were filtered. The crude crystals were dissolved into 300 ml of methyl isobutyl ketone, then washed 3 times with 100 ml of 5% aqueous solution of sodium hydroxide. The crude crystals obtained by condensing the methyl isobutyl ketone solution were purified by column chromatography wherein a mixed solvent consisting of 5 parts toluene and 2 parts ethyl acetate is used as the developing solvent. Each effluents of the developing solvent were condensed, affording the compounds having substituents represented by the formulas (II) and (III), which are 18 g of 4-(α-(hydroxymethyl)benzyloxy)-4'-benzyloxydiphenyl sulfone (Compound 1-2) of which melting point being from 120° C. to 122° C. in a form of whitish crystals, and 7 g of 4-(β-hydroxyphenethyloxy)-4'-benzyloxydiphenyl sulfone (Compound 2—2) of which melting point being from 138° C. to 140° C., in a form of whitish crystals, respectively.

EXAMPLE 4

(Example of the synthesis of Compound 1—1)

To 250 ml of methyl isobutyl ketone were added 50 g of 4,4'-dihydroxydiphenyl sulfone, 16 g of styrene oxide and 1 ml of N-benzyl-N-ethylaniline, then the mixture was heated to reflux to react for 10 hours. The reacted mixture was cooled, then washed with saturated aqueous solution of sodium carbonate to remove the unreacted raw materials. Then the product was extracted with 200 ml of 4% aqueous solution of sodium hydroxide to separate the water layer. The water layer was acidified with 10% hydrochloric acid to obtain 7 g of the crude crystals. According to the analysis of the crude crystals by liquid chromatography, it was found that most of the crude crystals was the compound having a substituent of the formula (II), and the compound having a substituent of the formula (III) was not detected therein. Then the crude crystals was recrystallized in 30 ml of ethyl acetate, affording 6 g of 4-(α-(hydroxymethyl)benzyloxy)-4'-hydroxydiphenyl sulfone having a substituent represented by the formula (II) in a form of whitish crystals, of which melting point is from 194° C. to 196° C.

This process can selectively manufacture the compounds having the substituents represented by the formulas (II) and (III) by using a tertiary amine as a catalyst even if styrene oxide derivatives are used as the raw material.

EXAMPLE 5

(Example of the synthesis of Compound 1—1, Alternative method)

160 ml of water, 12 g (0.3 mol) of sodium hydroxide, 50 g (0.2 mol) of 4,4'-dihydroxydiphenyl sulfone (hereinafter "BPS") and 250 ml of diethyl ketone were placed into 500 ml flask. Then 12 g (0.1 mol) of styrene oxide was further added thereto, and the mixture was heated to reflux to react for 4 hours. After the completion of the reaction, the mixture was acidified with dilute sulfuric acid to separate the water layer. The organic solvent layer was washed with 5% aqueous solution of sodium carbonate to recover the unreacted BPS, then extracted twice with 100 ml of hot 3% aqueous solution of sodium hydroxide. The organic solvent layer separated was discarded, and the water layer was acidified with dilute hydrochrolic acid to obtain 31.8 g of the crude objective compound. The purity thereof was 83% by liquid chromatography.

The crude product was then added with 250 ml of ethyl acetate and heated to reflux for 30 minutes. After cooling the solution, the crystals were precipitated, filtered and dried to obtain 19.8 g of purified 4-(α-(hydroxymethyl)benzyloxy)-4'-hydroxydiphenyl sulfone in a form of whitish crystals, of which melting point is from 194° C. to 196° C. The purity thereof was 99.3% by liquid chromatography, and the yield from the raw material BPS was 54%.

EXAMPLE 6

(Preparation of Thermal Sensitive Recording Paper using the Compound of the Formula (I) as Adjuvant)

| Chromogen dispersion (Liquid A) | |
| --- | --- |
| 3-dibutylamino-6-methyl-7-anilinofluorane | 7.0 g |
| 15% polyvinyl alcohol aqueous solution | 30.0 g |
| Filler (Calcium carbonate) | 13.5 g |
| Purified water | 49.5 g |
| Color developer dispersion (Liquid B-1) | |
| 2,2-bis(4-hydroxyphenyl)propane | 7.0 g |
| 15% polyvinyl alcohol aqueous solution | 30.0 g |
| Filler (Calcium carbonate) | 13.5 g |
| Purified water | 49.5 g |
| Color developer dispersion (Liquid B-2) | |
| 4-hydroxy-4'-isopropoxydiphenyl sulfone | 7.0 g |
| 15% polyvinyl alcohol aqueous solution | 30.0 g |
| Filler (Calcium carbonate) | 13.5 g |
| Purified water | 49.5 g |
| The invented compound dispersion (Liquid C) | |
| A compound of the invention | 7.0 g |
| 15% polyvinyl alcohol aqueous solution | 30.0 g |
| Filler (Calcium carbonate) | 13.5 g |
| Purified water | 49.5 g |
| Filler dispersion (Liquid D) | |
| Filler (Calcium carbonate) | 20.5 g |
| 15% polyvinyl alcohol aqueous solution | 30.0 g |
| Purified water | 49.5 g |

Each mixtures of the compositions recited above were sufficiently grinded by using sand grinder to prepare Liquid A, Liquid B-1 or B-2, Liquid C and Liquid D. One part by weight of Liquid A, 2 parts by weight of Liquid B-1 or B-2 and one part by weight of Liquid C were mixed to prepare a coating liquid. The coating liquid was coated on white papers by using Wire Rod No. 12 and dried, then calendered by Calendering machine to prepare two groups of thermal sensitive recording papers, which are thermal sensitive recording paper-1 comprising Liquid B-1 group and thermal sensitive recording paper-2 group comprising Liquid B-2. These thermal sensitive recording papers are examples that the compound of the invention is used as an image stabilizing agent.

Comparative Example 1

The thermal sensitive recording paper-1 group without containing the compound of this invention was prepared according to the procedure described in the example 6 wherein the Liquid B-1 was selected and Liquid D was used instead of Liquid C.

Comparative example 2

The thermal sensitive recording paper-2 group without containing the compound of this invention was prepared according to the procedure described in the example 6 wherein the Liquid B-2 was selected and Liquid D was used instead of Liquid C.

EXAMPLE 7

(Test on Resistance of Thermal Sensitive Recording Paper against Plasticizers)

The thermal sensitive recording paper-1 group and the paper-2 group prepared in the example 6, the comparative example 1 and 2 were colored to be mosaic pattern under the condition of 22 volts of impressed printing voltage and 1.8 ms of pulse width by Test Apparatus for Color Development of Thermal Sensitive Paper (Ohkura Denki Co., Ltd. Type TH-PMD), then a lap film made of vinyl chloride was closely touched over the surface colored. Under such and the following conditions, test on resistance of the recording paper to plasticizers was conducted.

Condition 1: To allow the paper to stand for 24 hours under an atmosphere at about 40° C.

Condition 2: To allow the paper to stand for 7 days at room temperature.

The color density of the papers before and after exposing them to the above treatments were determined by Macbeth Reflection Densitometer RD-514 (Filter used: #106). The results are shown in Table 3.

TABLE 3

| Thermal Sensitive Recording Paper Group | Before Treatment Value | Resistance to Plasticizers | | | |
|---|---|---|---|---|---|
| | | 40° C. 24 hrs. | | Room Temp. 7 days | |
| | | Value | Ratio Remained | Value | Ratio Remained |
| Thermal sensitive recording paper-1 | | | | | |
| Compound 1-1 | 1.16 | 0.43 | 37.1% | 0.80 | 69.0% |
| Compound 1-2 | 1.10 | 0.23 | 20.9% | 0.33 | 30.0% |
| Compound 2-1 | 1.14 | 0.40 | 35.1% | 0.65 | 57.0% |
| Compound 2-2 | 1.10 | 0.23 | 20.9% | 0.34 | 30.9% |
| Comparative example 1 | 1.08 | 0.16 | 14.8% | 0.21 | 19.4% |
| Thermal sensitive recording paper-2 | | | | | |
| Compound 1-1 | 1.18 | 0.92 | 78.0% | 1.03 | 87.3% |
| Compound 2-1 | 1.19 | 0.82 | 68.9% | 1.05 | 88.2% |
| Comparative example 2 | 1.14 | 0.28 | 24.6% | 0.54 | 47.4% |

The values shown in the above table indicate that the greater the value showed, the higher the color density became. Further, the greater ratio remained indicates less decoloring. The results validate that the colored image developed on the thermal sensitive recording paper using the compounds of this invention together with a color developer is excellent in resistance to plasticizers. For the calculation of the ratio remained, the percentage for the ratio remained was calculated by dividing the color density values after the exposure by those of before the exposure.

EXAMPLE 8

(Test on Oil Resistance of Thermal Sensitive Recording Paper)

The thermal sensitive recording paper-1 group and the paper-2 group prepared in the example 6, the comparative example 1 and 2 were colored to be mosaic pattern according to the procedure described in the example 7. To the colored surface was attached 1 μl of 10% salad oil solution in n-hexane by using microsyringe. After volatizing the solvent n-hexane, the recording paper was placed in a light-shielded box, then allowed it to stand for 7 days.

The color density of the papers before and after exposing them to the above treatments were determined by Macbeth Reflection Densitometer RD-514 (Filter used: #106). The results are shown in Table 4.

TABLE 4

| Thermal Sensitive Recording Paper Group | Before Treatment Value | After Treatment of Oil Room Temperature, 7 Days | |
|---|---|---|---|
| | | Value | Ratio Remained |
| Thermal sensitive recording paper-1 | | | |
| Compound 1-1 | 1.16 | 1.01 | 87.1% |
| Compound 1-2 | 1.10 | 0.77 | 70.0% |
| Compound 2-1 | 1.14 | 0.95 | 83.3% |
| Compound 2-2 | 1.10 | 0.62 | 56.4% |
| Comparative example 1 | 1.08 | 0.24 | 22.2% |
| Thermal sensitive recording paper-1 | | | |
| Compound 1-1 | 1.18 | 1.17 | 99.2% |
| Compound 2-1 | 1.19 | 1.15 | 96.6% |
| Comparative example 2 | 1.14 | 0.70 | 61.4% |

As described hereinbefore, the greater values shown in the above table indicate higher color density. Further, the greater ratio remained indicates less decoloring. The results validate that the colored image developed on the thermal sensitive recording paper using the compounds of this invention together with a color developer is excellent in oil resistance.

EXAMPLE 9

(Preparation of Thermal Sensitive Recording Paper comprising the Compound of the Formula (I) as Color Developing Agent)

A thermal recording paper was prepared according to the procedure of the example 6 wherein the dispersion of the example 6 and a coating liquid prepared of 1 part by weight of Liquid A and 2 parts by weight of Liquid C were used.

TABLE 6

| Color Developer for Thermal Sensitive Recording Paper | Background | | | Colored Image | | |
| --- | --- | --- | --- | --- | --- | --- |
| | Before Treatment | Resistance Humidity /Heat | Light Resistance | Before Treatment | Resistance Humidity /Heat | Light Resistance |
| Compound 1-1 | 0.05 | 0.06 | Y0.12 | 1.12 | 1.16 | 1.05 |
| Comparative example 1 | 0.07 | 0.09 | Y0.13 | 1.30 | 1.30 | 1.26 |

This recording paper is an example which use the compound of the formula (I) wherein $R^1$ is hydrogen, as the color developing agent.

EXAMPLE 10

(Test on Thermal Sensitive Recording Paper using The Compound of the Invention as the Color Developing Agent)

Each thermal sensitive recording paper prepared according the procedure described in the example 9 and the comparative example 1 was imposed to develop color so as to be mosaic pattern in the manner as described in the example 7, then carried out the test on resistance to plasticizers under the condition that the recording papers are allowed to stand for 4 and 8 hours in an atmosphere at about 40° C.

Moreover, each of the thermal sensitive recording papers prepared in the example 9 and the comparative example 1 were heated to develop color at 150° C. up to the saturated condition by using dry heating tester (Kishino Science Machinery Co., Type E-3). Resistance test against humidity and heat (80% RH, 50° C., 24 hours) and light resistance test (Carbon Arc Fedemeter, 4 hours) were carried out for the background and the colored images.

The color density of the papers before and after exposing them to the above treatments were determined by Macbeth Reflection Densitometer RD-514 (Filter used: #106, for light resistance test only: #47). The results are shown in Tables 5 and 6.

TABLE 5

| Thermal Sensitive Recording Paper Group | Before Treatment Value | Resistance to Plasticizers | | | |
| --- | --- | --- | --- | --- | --- |
| | | 4 hours | | 8 hours | |
| | | Value | Ratio Remained | Value | Ratio Remained |
| Compound 1-1 | 0.92 | 0.78 | 84.8% | 0.65 | 70.7% |
| Comparative example 1 | 1.11 | 0.43 | 38.7% | 0.28 | 25.2% |

It is obviously shown in Table 5, as well as described in Table 4, that the colored image developed on the thermal sensitive recording paper using the compounds of this invention as the color developer has better resistance to plasticizers than that of the paper using a color developer 2,2-bis(4-hydroxyphenyl)propane only.

Table 6 indicated that the compound of the invention is superior as a color developer and better than a commercially available color developer, 2,2-bis(4-hydroxyphenyl)propane, in terms of the clearness of the background.

INDUSTRIAL APPLICABILITY

The present invention is directed to novel compounds which improve the long term stability of the developed image, particularly resistance against plasticizers, and recording materials applying the compound. For example, the recording materials can retain the colored images very stably even under the condition that the colored images contact to packaging materials made of organic polymeric compounds. Additionally, the images developed on the recording material using the compound of the invention does not undergo the change of color such as the change from black to dark green, maintaining the true color tone of the leuco chromogen used.

In addition thereto, the compound of the invention has color developing activity being in no way inferior to common color developers at the same time, so that the compound is also useful as a color developer superior in giving long term stability for colored images.

What we claim is:

1. A phenethyl alcohol derivative represented by the general formula (I):

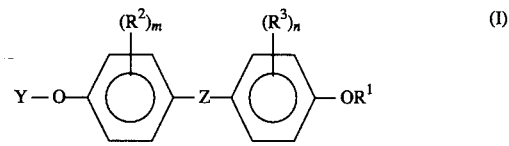

(I)

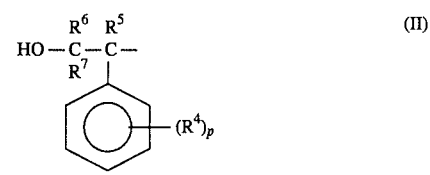

(II)

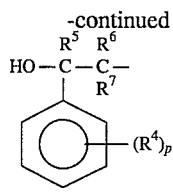

wherein Y is a substituent represented by the formula (II) or (III),

R¹ is hydrogen, lower alkyl or unsubstituted aralkyl or aralkyl substituted by halogen, nitro, alkyl having 1 to 5 carbon atoms or alkoxy having 1 to 5 carbon atoms, R², R³ and R⁴ are each independently halogen, nitro, lower alkyl, lower alkoxy, lower alkenyl or lower alkenyloxy, R⁵, R⁶ and R⁷ are independently hydrogen or lower alkyl, Z is —SO₂—, —CO—, —C(CH₃)₂—, —S—, or —O—, m, n and p denote independently 0 or an integer from 1 to 4, with the proviso that each substituents represented by R², R³ and R⁴ may be different from one another when all of m, n and p are an integer 2 or more.

2. A phenethyl alcohol derivative of the formula (I) according to claim 1 wherein the substituent Z is —SO₂—, or —CO—.

3. A phenethyl alcohol derivative of the formula (I) according to claim 1 represented by the following formula:

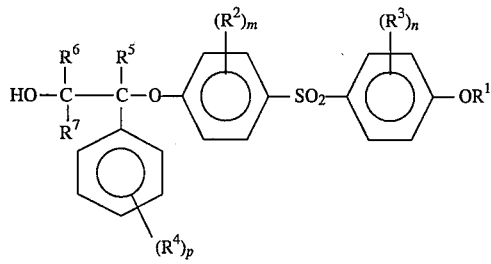

wherein R¹, R², R³, R⁴, R⁵, R⁶, R⁷, m, n, and p are as defined in claim 1.

4. 4-(α-(hydroxymethyl)benzyloxy)-4'-hydroxydiphenyl-sulfone.

5. A phenethyl alcohol derivative of the formula (I) according to claim 1 represented by the following formula:

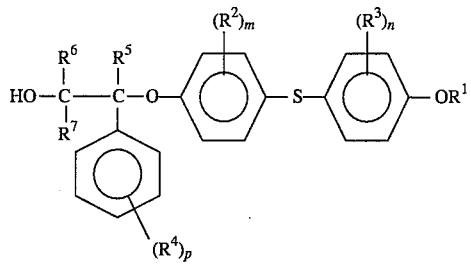

wherein R¹, R², R³, R⁴, R⁵, R⁶, R⁷, m, n and p are as defined in claim 1.

6. A phenethyl alcohol derivative of the formula (I) according to claim 1 represented by the following formula

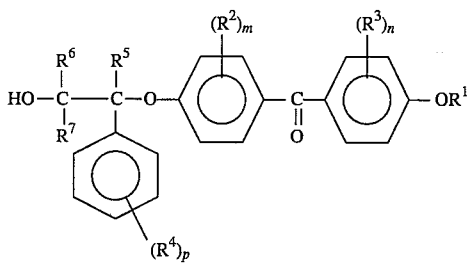

wherein R¹, R², R³, R⁴, R⁵, R⁶, R⁷, m, n and p are as defined in claim 1.

7. A phenethyl alcohol derivative of the formula (I) according to claim 1 wherein aralkyl is benzyl or phenethyl.

* * * * *